Figure 1:
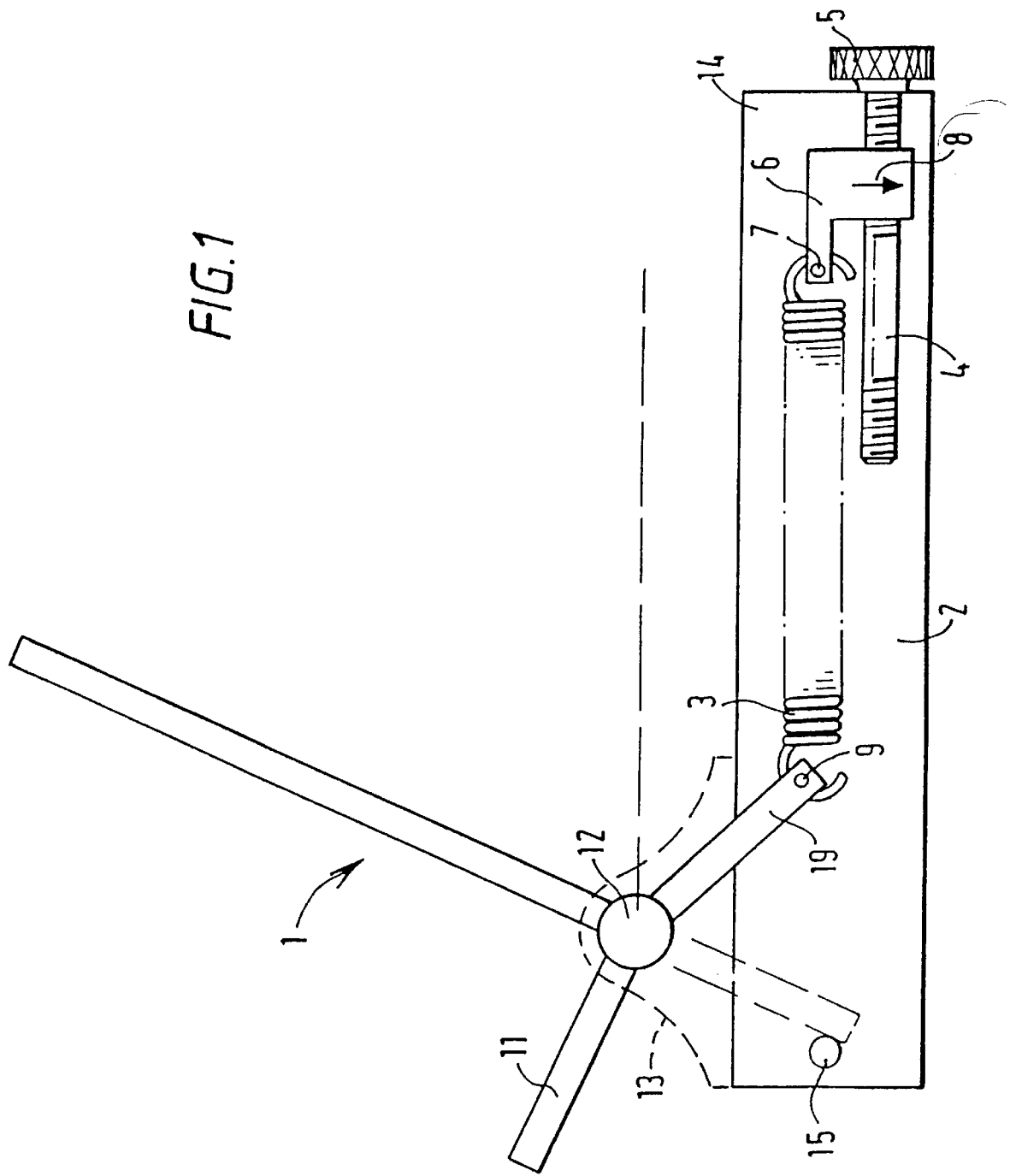

United States Patent [19]
Patchett et al.

[11] Patent Number: 5,803,907
[45] Date of Patent: Sep. 8, 1998

[54] PERIPHERAL VASCULAR DISEASE TESTING

[75] Inventors: Kim Patchett, Auvernier, Switzerland; Stuart Wallace, Frinton-on-Sea, Great Britain

[73] Assignee: Stu-Ert Medical Devices Limited, Essex, United Kingdom

[21] Appl. No.: 557,021

[22] PCT Filed: Jun. 3, 1994

[86] PCT No.: PCT/GB94/01217

§ 371 Date: Mar. 5, 1996

§ 102(e) Date: Mar. 5, 1996

[87] PCT Pub. No.: WO94/28794

PCT Pub. Date: Dec. 22, 1994

[30] Foreign Application Priority Data

Jun. 8, 1992 [GB] United Kingdom .................. 9311816
Mar. 29, 1994 [GB] United Kingdom .................. 9406174

[51] Int. Cl.$^6$ ..................................................... A61B 5/02
[52] U.S. Cl. ......................... 600/301; 600/483; 600/485; 600/488; 600/490; 600/500; 600/501; 600/502; 600/507; 600/526
[58] Field of Search ................................. 128/687, 688, 128/691, 693, 694, 672; 600/301, 483, 485, 488, 490, 500, 501, 502, 507, 526

[56] References Cited

U.S. PATENT DOCUMENTS

| | | |
|---|---|---|
| 4,280,486 | 7/1981 | Hofstein . |
| 4,454,885 | 6/1984 | Reddy . |
| 4,476,874 | 10/1984 | Taenzer et al. . |
| 4,502,680 | 3/1985 | Blum et al. . |
| 4,556,066 | 12/1985 | Semrow . |
| 4,732,038 | 3/1988 | DelGiorno et al. . |
| 4,790,325 | 12/1988 | Lee . |
| 5,058,592 | 10/1991 | Whisler . |
| 5,090,421 | 2/1992 | Wagoner, III . |

FOREIGN PATENT DOCUMENTS

| | | |
|---|---|---|
| 0 016 399 | 3/1980 | European Pat. Off. . |
| 0 232 507 | 12/1986 | European Pat. Off. . |
| 0 330 463 | 2/1989 | European Pat. Off. . |
| 0 467 853 A1 | 7/1991 | European Pat. Off. . |
| 69.35282 | 10/1969 | France . |
| 89 09 993 U | 2/1990 | Germany . |
| WO 88/08276 | 11/1988 | WIPO . |
| WO 92/07508 | 5/1992 | WIPO . |

*Primary Examiner*—Mickey Yu
*Assistant Examiner*—Dinh X. Nguyen
*Attorney, Agent, or Firm*—Woodcock Washburn Kurtz Mackiewicz & Norris LLP

[57] ABSTRACT

The present invention provides an diagnostic apparatus and method for physiologically measuring the biological responses of a selected group of muscles during exercise. Biological responses measured include blood flow, blood pressure, transcutaneous oxygen, and lymphatic clearance rate. The apparatus comprises a pressure plate attached to an axle. A spring mechanism is attached to the pressure plate to bias the plate towards the resting position. The spring may be adjusted so as to increase the resistance to the group of muscles being exercised and induce fatigue.

30 Claims, 6 Drawing Sheets

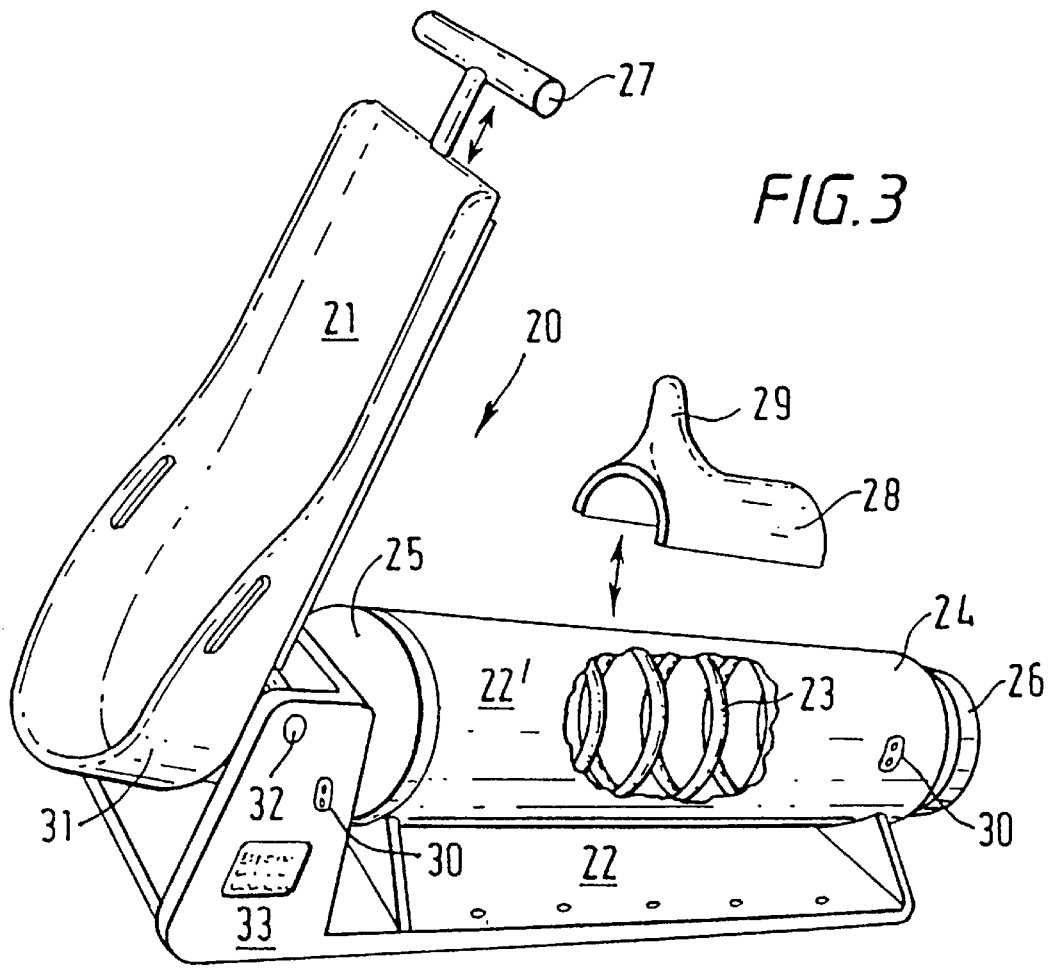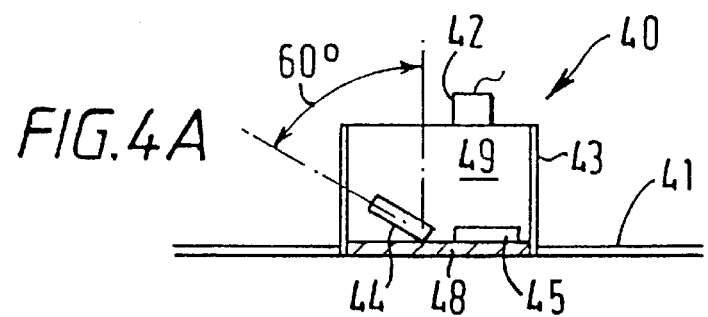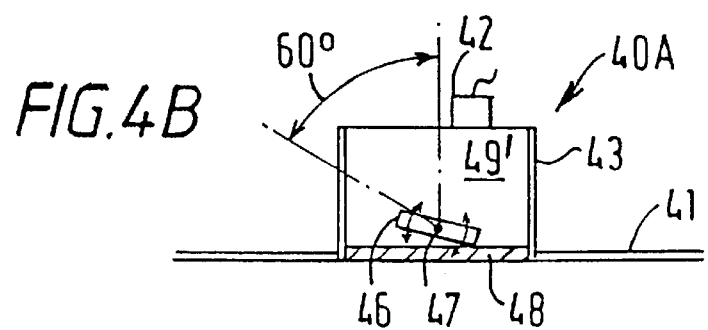

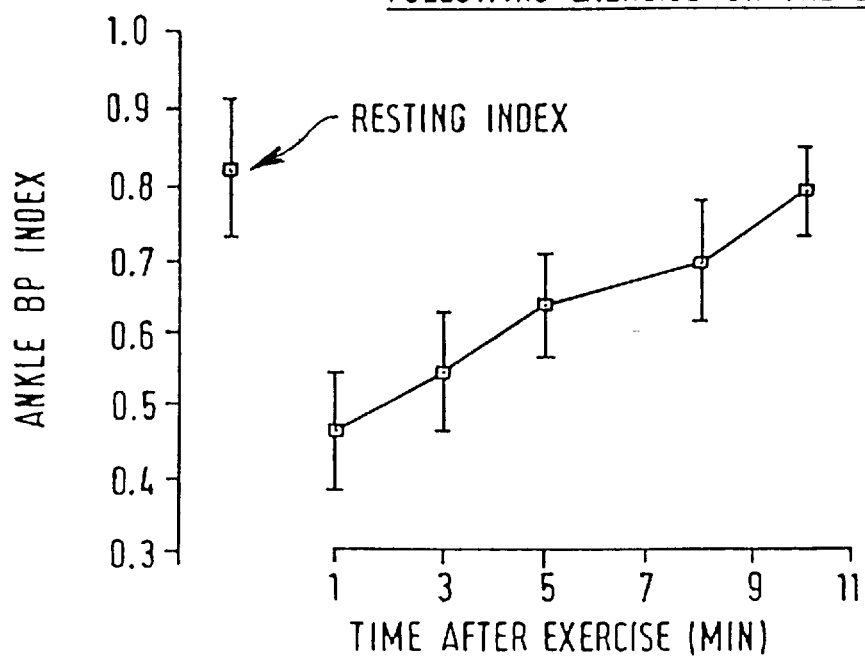
FIG. 8  CHANGE IN ANKLE BRACHIAL PRESSURE INDEX FOLLOWING EXERCISE ON TREADMILL.
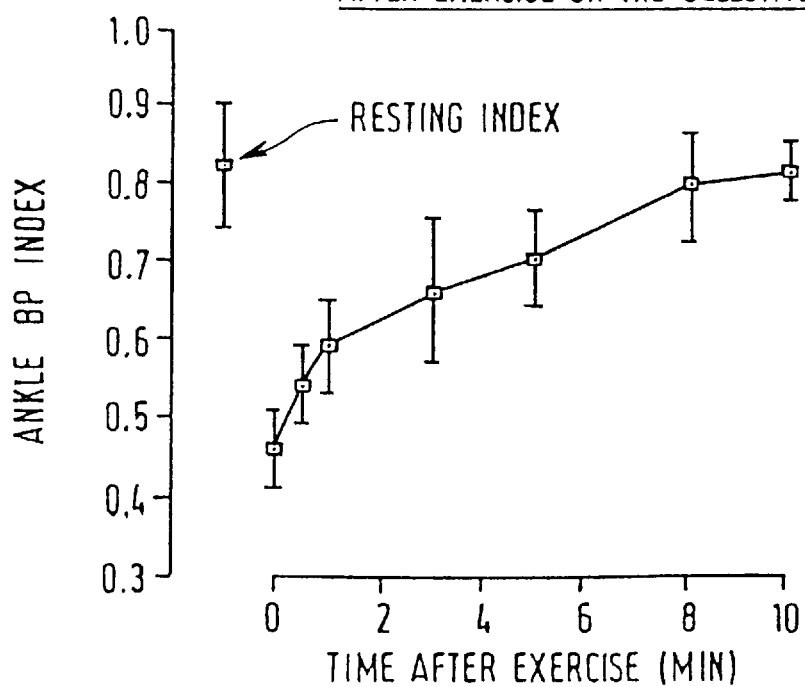
FIG. 9  CHANGE IN ANKLE BRACHIAL PRESSURE INDEX AFTER EXERCISE ON THE SELECTIVE EXERCISE DEVICE.

PERIPHERAL VASCULAR DISEASE TESTING

The present invention relates to peripheral vascular disease testing and particularly to an apparatus and method for (1) screening patients for further study, and (2) investigating in greater detail, and more accurately, patients who are known to have peripheral vascular disease and may be either under observation or have had angioplasty or an operation.

It is an ongoing problem that patients present to General Practitioners with symptoms of their limbs which could indicate either an orthopaedic, neurological, or a vascular problem. For example, arterial problems of the lower limb can present as walking pain, rest pain, cold feet, skin changes and weak or absent pulses. Some of these features can well be due to orthopaedic, or neurological problems and it is difficult for the General Practitioner, or specialists in other branches of medicine to know to whom to refer the patient in such circumstances.

Decisions regarding the treatment of peripheral arterial disease of the lower limb, while based on the clinical features, may be clarified by non-invasive investigations. Absent pulse(s) in the leg, alone, are enough to determine the presence of arterial disease, and non-invasive tests are not necessary to make the a diagnosis. They may be used however to document the presence and extent of a disease. If pedal pulses are weak, a non-invasive tests are also unnecessary but they can provide objective quantitive confirmation. The ankle pressure at rest is simple to measure, confirms the clinical impression, and is particularly useful in obese patients or if there is ankle oedema that makes the pulses difficult to feel. If the pulses are normal, however, and the patient has had pain on walking, further tests are necessary. In such patients the ankle pressure should be measured at rest and after exercise because in the presence of a non-occlusive stricture, there may be normal ankle pressures at rest, and a fall in ankle pressure after exercise.

The use of doppler and doppler wave form analysis is now a standard investigation technique for patients with possible circulatory disorders of the limbs. Investigation is performed before and after exercise; which exercise has always been standardised by using a treadmill or similar apparatus.

There are a number of disadvantages for the utilisation of the treadmill in addition to cost and these may be characterised without limitation as follows:

1. They can be difficult to walk upon, particularly for the elderly;
2. Assessment cannot be made in patients with other conditions affecting the limb, e.g. osteo-arthritis of the hip;
3. The "whole patient" is exercised and there would is a rise in cardiac output etc. which can significantly alter the results. Also by exercising the "whole patient" those with cardiac disease (manifested by previous M.I., angina or asymptomatic) are at risk of over-exercising and consequent stress.
4. The cardiac patient may be limited by angina or shortness of breath before leg pain occurs.
5. Assessment cannot be made in amputees;
6. Assessment cannot be made in the early post-operative period;
7. Assessment cannot be made of a limb in isolation;
8. Assessment may be difficult in elderly, frail patients who may be partially sighted or who would otherwise experience problems utilising a treadmill.
9. Assessment may be difficult in blind, diabetic, neuropathic, or those with vertebrabasilar disease with a treadmill since they are unable to perform dynamic assessments (angiograph duplex).
10. It is not possible to exercise the arms utilising a treadmill.
11. There is a time delay in doppler measurement after use of a treadmill occasioned by the time it takes the patient to return to the couch for testing. This means that accurate testing of old and infirm patients becomes problematic.

Since the onset of vascular disease tends to occur in the elderly, and since the elderly are likely to have at least one of the conditions referred to above, the treadmill, even if available, is of limited use in diagnosis in these cases.

The applicant has now discovered that the blood flow rate measurable in the distal circulation, utilising for example, a Doppler probe, remains normal or elevates after exercise in a limb with a normal blood flow. However, blood pressure falls, or even reaches zero, in a limb with abnormally impaired blood flow. It will be appreciated that by exercising just the group of muscles associated with the limb concerned, the overall heart rate is not much affected (up to about 20%) and hence not only can the diagnostic method be carried out upon the frail and elderly more easily, but the results obtained relate more directly to the limb under test. Similarly, by exercising one limb, measurement can be made in the non-exercised limbs.

The applicant has devised a simple non-invasive technique to assist not only the vascular specialist in more detailed analysis of the disease before and after treatment, but also to assist the General Practitioner in diagnosis. Further, with instruction a patient can perform self-assessment at home as now happens with blood pressure monitoring.

Accordingly, the invention provides in one aspect a diagnostic apparatus comprising a standardizable resistance means to resist a force applied thereto by a group of limb muscles during exercise, and test means for physiologically measuring a biological component resultant from said limb exercise. The biological component may be selected from one or more of blood flow, blood pressure, transcutaneous oxygen and lymphatic clearance rate. Where the resting blood flow is measured before and after exercise with the standardizable resistance means, if there is a vascular obstruction in the limb the blood flow will markedly fall or even reach zero. Similarly transcutaneous oxygen values will fall. The device may also be used to test lymphatic clearance of an injected labelled nucleotide before and after limb exercise.

Measurements that can be made before and after exercise, in addition to blood flow by Doppler include for example transcutaneous oxygen measurements, compartmental pressures, leg volumes and other measurements that can be readily monitored.

It will be appreciated that vascular disease tends to show up at or towards the ankle and lower calf muscles because these are furthest from the heart. However, asymptomatic vascular disease can also be present in the other limbs and an estimation of the disease in these limbs allows a more accurate diagnosis as to whether, for example, by-pass surgery is likely to be more effective than drug therapy.

The utilisation of the device in accordance with the present invention allows different groups of muscles to be exercised. For example, the standardizable resistance means may be a spring biased pivoted plate preferably with a heel rest. By altering the disposition of the heel rest of the device (as to be described later), relative to the pivotal point of the device, it is possible to alter the form of the work done by the limb muscles, for example the calf muscles, so as to show up particular deficiencies in the vascular system in associated arteries. It is preferred however to adjust the heel rest so that on average the pivot point is juxtaposed to the axis of the leg.

The resistance means is preferably such as to resist multiple motions to induce fatigue by using up oxygen and available nutrients in the limb that has an inadequate blood supply.

Various exercise devices have been described in the prior art for the purpose of exercising various groups of muscles. In general these are complex pieces of equipment which provide output data for computer analysis. Not only does this facility add markedly to the cost of such devices, it is inaccurate and is not in fact necessary with the arrangement of the present invention.

Thus, for example, EP-A-0430067 discloses a device for exercising the leg muscles against a known force. The apparatus is complex and would be difficult to utilise with the upper limb.

WO 88/08276 reveals a muscle testing apparatus for testing the strength of muscles or groups of muscles. Again data is taken direct from the apparatus itself, and although it exercises groups of muscles the data taken cannot be directed specifically to the presence or absence of vascular disease.

U.S. Pat. No. 5,090,421 reveals an apparatus for testing muscular strength utilising a pressure plate and a pressure transducer. Similarly U.S. Pat. No. 4,732,038 reveals the interposing of a force sensing device within a range of motion of a limb or other body part to sense the flexion of a selected group of muscles. Again, in each case data from said flexion is collected from the device itself rather than, as in the instance of the present invention, the device being utilised essentially to induce fatigue on a controlled basis.

With adaptions all the foregoing devices would be suitable for use in the present invention in some respects, but only in so far as they allowed the controlled fatiguing of a group of muscles, which is not the purpose for which any of these devices have been designed.

In a preferred form of resistance means in accordance with the present invention there is provided a standardized resistance device for a diagnostic apparatus, said device comprising a plate pivoted about an axle, spring means operatively connected to said plate to bias the plate to an at rest position, and adjustment means for preloading the spring to a desired value; whereby in use the plate may be reciprocated by a limb against the spring bias to induce fatigue in the limb on a standardized basis.

The device may comprise a base supporting the axle and enclosing or supporting the adjustment means. The adjustment means may be a screw thread and the spring may be a tension spring. The adjustment means may include a screw threaded block connecting the screw thread to the tension spring, and indicator means may be provided to indicate a range of spring tension values, for example high, medium or low, or delineated in Kg, for example. With small design adjustments a compression spring may be similarly utilized.

The patient may, in use, press the plate to the end of its travel a set number of times, or may continue working on the pressure plate until fatigue or claudication sets in, before blood flow is remeasured.

The means for physiologically testing blood flow is preferably a Doppler Ultrasound blood flow rate monitoring device, for example that sold under the Registered Trade Mark "Dopplex". It is known that resting arterial and venous blood flow rate measurements provide characteristic doppler wave forms when measured at various sites with a hand held problem containing a terminal transducer. For example, the normal blood flow rate in the common femoral artery is tri-phasic in that it has a positive wave form in the systolic flow phase followed by a negative flow rate in the reverse flow phase followed by a third phase of positive flow before the next systole.

Partial stenosis of the common femoral artery will reduce the readings for the first systolic flow phase and the reverse phase and may result in the disappearance of the third phase altogether. Severe stenosis results in the reverse phase disappearing as well. Similar wave forms for other areas in the limb, and for the venous system, are also known in the art to have characteristic signatures.

Whereas this technology is known and is useful for the Consultant, it is beyond the normal competence of a General Practitioner or paramedic to accurately interpret such blood flow measurements. However, a change from a positive blood flow to a significantly lower blood flow, or no significant blood flow at all, is a reading which can be confidently interpreted on a straight forward basis by a paramedic and allow an accurate diagnosis at least between orthopaedic, neurological, and vascular problems.

Further with this device a patient can be made to exercise against a gradient which is beneficial to diabetic patients with rigid, non-collapsible vessels.

The apparatus in accordance with the present invention may also be arranged such that the arc of travel of the pressure plate is adjustable and/or the apparatus provides means indicative of the load applied. The spring means may be operatively associated with a signal generating means indicative of each completed movement whereby work done can be readily calculated. The spring means may be associated with a permanent magnet and a hall effect sensor thereby to generate an output signal for each completed stroke of the pressure plate. Further a second hall effect device can be used to define the position of the remote end of the spring means so that spring loading can be readily measured by electronic means. This enables the audible or visual signal to be produced when a patient has completed a given quantity of work. This enables ready comparison with other patients and normal volunteers. The pressure plate may further comprise an extendable handle and the base may comprise an elbow restraint means on the upper surface thereof; whereby in use the device may be utilised to exercise the arm.

A further improvement in accordance with the present invention additionally lies in the problem that after exercise has been taken, a certain period lapses before a hand held Doppler probe, for example, can be correctly positioned to measure pressure and flow rate in a artery. This is particularly so where the pressure and flow rate are low as is likely to be the case after claudication. Accordingly in a further aspect of the present invention the applicant provides a specially adapted Doppler transducer assembly which can be secured to the skin in a correct position and used prior to, during, and after exercise. In order to use the Doppler transducer assembly in accordance to the present invention during exercise it is usually necessary to briefly suspend the exercise so that readings may be taken, alternatively readings may be taken continuously and a computer utilised to discount traces within certain limits so that only readings taken during said suspension are recorded and displayed.

The applicants have found the key to successfully positioning a Doppler transducer of the type useful in the present invention is to ensure that it is correctly positioned over the desired artery. In the first place it is desirable therefore to mark, with a standard Doppler probe, the position of the artery on the skin with a marker pen. This mark may also include the precise direction of the artery.

It follows that a housing secured over the mark with the marker pen should be hollow so that the mark can be seen clearly through the housing.

In the present invention two transducers are utilised one to monitor flow and the other to monitor pressure. It is important that these are correctly positioned relative to the artery so that the flow transducer i.e. the 60° transducer, is directed along the axis of the artery. For this reason the transducer should be rotatable in the housing as well as being secured therein. This can be achieved by providing a flow line on the transducer housing so that it may be rotated into accord with the line applied earlier, and for it to be either an interference fit in the housing or to be screwed thereinto so that relative rotation can occur.

The applicants have found further that in vascular determinations it is desirable to have both flow and pressure values available and this is much better achieved with a single Doppler array.

Various attempts have been made to secure a Doppler transducer to a skin surface so as to monitor blood flow parameters without having to hold a probe. One such arrangement is to be found in U.S. Pat. No. 4,556,066 which provides a single transducer disposed in an ultrasound acoustic pad. The pad has a circular retaining member to hold the piezo electric transducer perpendicular to the axis of a blood vessel; a strip of acoustic gel being disposed between the transducer and the skin. The circular bandage is adapted to overlay the assembly and to retain the transducer in contact with the skin. The problem with this is that it is difficult to correctly position the transducer over the artery because any markings cannot be seen once the transducer has been placed upon the skin. Further the overlaying bandage tends to subject the transducer into small lateral movements during the fixing process and accordingly the transducer will not always be effectively operational.

Similarly U.S. Pat. No. 5,058,592 relates to a similar acoustic pad but wherein the transducer is steerable. This is effected by providing an annular body with an adhesive foot to be secured to the skin and a moveable Doppler probe secured within the annulus and steered by means of being rocked into the correct position and held in position by means of a "VELCRO" tape. This arrangement tends to overcome the problem of faulty positioning because it is possible to see where the housing is going prior to securing the probe within the housing. However the device only measures blood pressure and provides no means whereby blood flow may be assessed or means for aligning the two so that the two components can be measured from the same position.

EP-A-467853 relates to a complex device comprising, inter alia, a sensor held in position by a cuff which extends over an extensive portion of the arm. This comprises a blood pressure and separately a blood flow monitoring device but these are not combined, they are not in a single skin patch and relative positioning clearly presents problems.

WO92/07508 similarly relates to a non-invasive arterial pressure monitor which comprises a pair of spaced Doppler transducers which both measure blood flow to achieve bi-directional flow determinations. There are no means for combining these two together or for measuring blood pressure discussed.

According therefore to a further specific aspect of the present invention there is provided a Doppler transducer assembly comprising a housing including a skin contact surface adapted to be releasable affixed to or held in contact with the skin, said housing supporting a Doppler transducer means adapted to output a signal when positioned at each of a plurality of stations, one of said signals being indicative of pressure and another of said signals being indicative of flow.

The Doppler transducer means may comprise at least two fixed transducers, first of said transducers being positioned substantially perpendicular to the skin contact surface of the housing and the second of said transducers been fixed at a predetermined angle relative thereto. The predetermined angle of said transducer may be at or about 60° to the skin contact surface of the transducer.

Alternatively the Doppler transducer means may comprise a transducer rotatable about its horizontal axis or oscillatable through a predetermined angle, said transducer being adapted to output a first signal indicative of pressure and a second signal indicative of flow. The housing may comprise means to drive the transducer such as an electric motor or oscillator means for example, an electromagnet. The housing may be square, rectangular, circular or ovoid in transverse cross-section and may be so arranged that the transducer assembly heads are recessed from the plane of the skin contact surface of the housing thereby to accommodate a Doppler wave transmitting gel.

The housing may be releasably retained on the skin either because the skin contact face of the housing is provided with an adhesive surface, or by the provision of a high friction surface associated with the resilient means for positioning about a body part to retain the housing in its operative position.

The Doppler transducer assemblies as just described may be utilised in conjunction with an automatic blood pressure cuff so that at periodic intervals during diagnosis said cuff is inflated, preferably in response to a predetermined cuff control signal, to allow blood pressure and flow rate to be automatically sampled. Although the assemblies in accordance to the present invention are particularly suited to utilisation with a dedicated microprocessor, the output signals obtained from the varied sources are at best collated and displayed on a computer monitor screen.

Finally there is provided a method for the non-invasive diagnosis of peripheral vascular supply to a limb, which method comprises establishing a resting vascular pressure or flow rate, utilising a limb to repeatedly move a standardised resistance over a predetermined distance for a set time or until claudication occurs, and establishing a post exercise pressure or flow rate. The limb may be the leg and the pre- and post-exercise vascular pressures may be denoted by an ankle pressure index as herein set forth. The vascular flow and/or pressure may be monitored during timed intervals during an exercise routine, and when a cuff is secured about the ankle it may be inflated, likewise at timed intervals during exercise, thereby to allow vascular flow and pressure values to be monitored during short resting periods during the exercise. Oximetry determinations may also be utilised in the arrangement in accordance with the present invention.

Signals from all the foregoing may be input to a neural network or other pattern recognition programme so that simple diagnoses can be computer generated.

Figure 2:
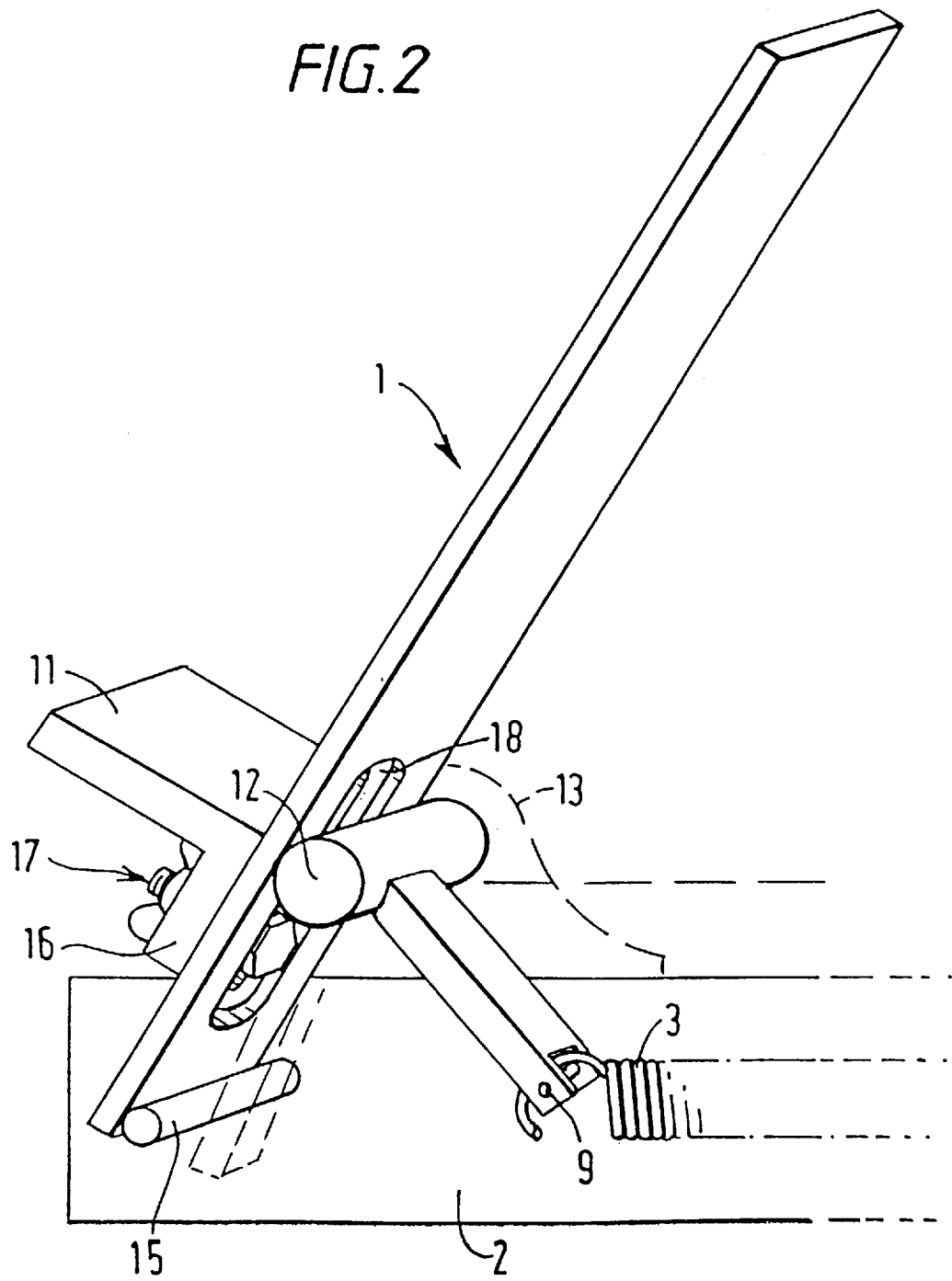

The invention will now be described, by way of illustration only, with reference to the following examples and the accompanying drawings in which:

FIG. 1 a side view in part cross-section of a standardizable resistance means for utilisation with the blood flow rate measuring device in accordance with a first aspect of the present invention, FIG. 2 shows a side view from beneath of a second alternative arrangement.

Figure 5:
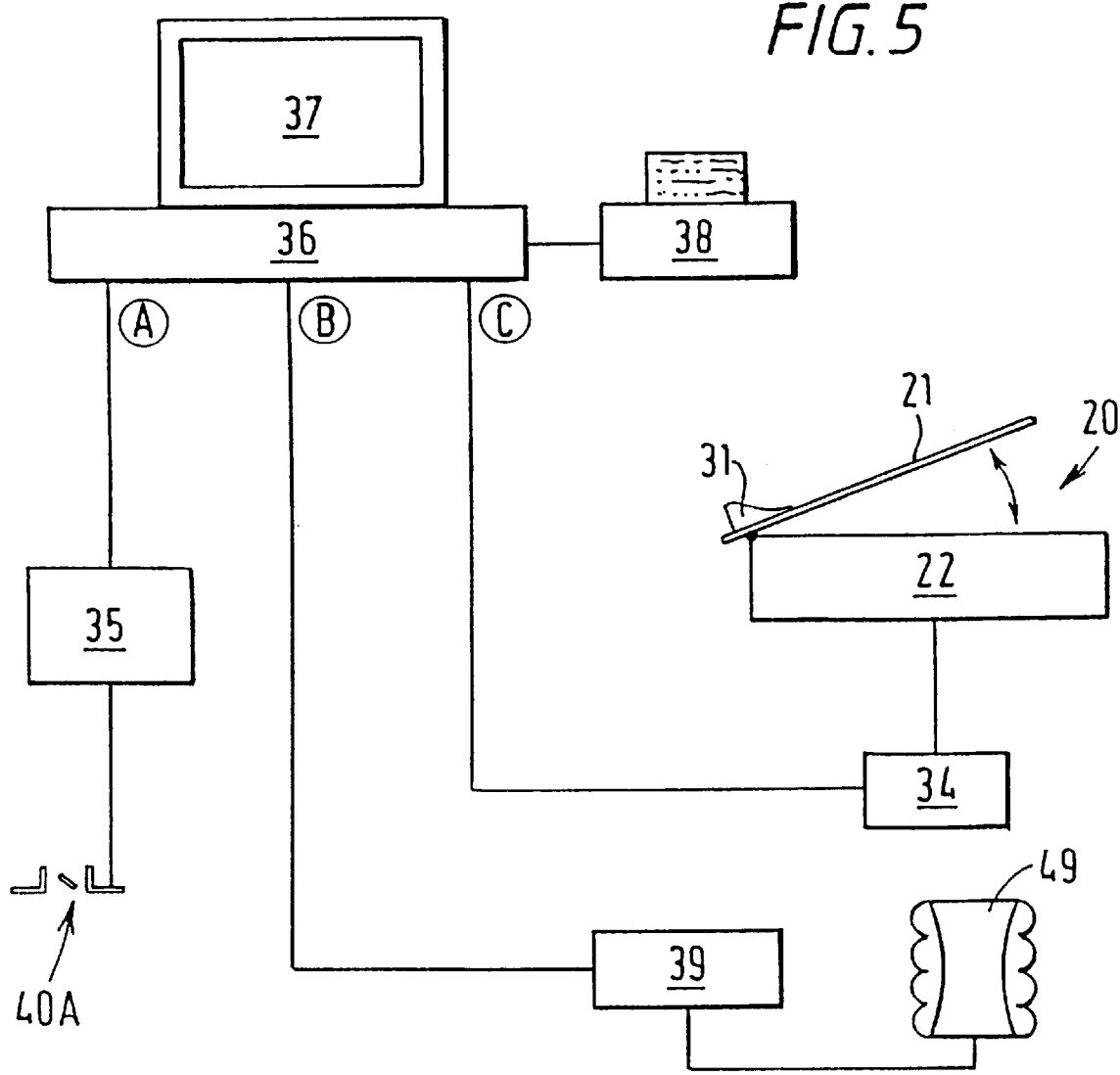
Figure 6:
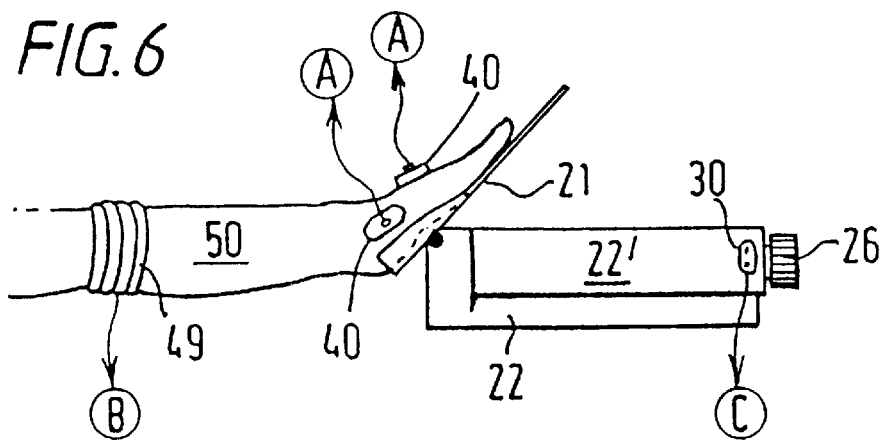
Figure 7:
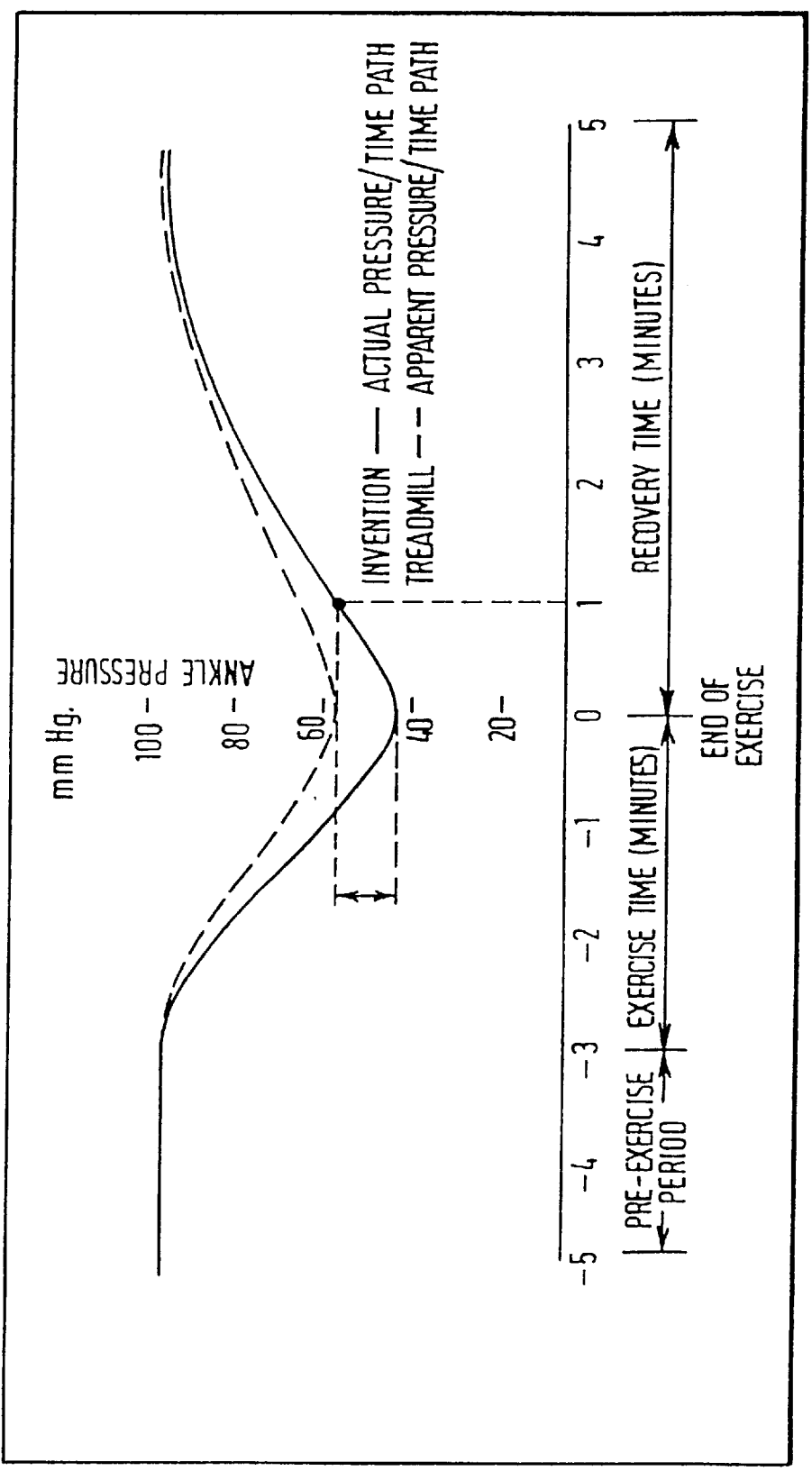

FIG. 3 shows a side view from above with part broken away of a third alternative standardizable resistance means for utilisation in accordance with the present invention, FIG. 4A shows a vertical diagrammatic cross-section through a Doppler transducer assembly in accordance to the present invention, FIG. 4B shows a vertical diagrammatic cross-section through a second form of Doppler transducer assembly in accordance to the present invention, FIG. 5 shows in diagrammatic form a computer controlled arrangement utilising the devices set out in FIGS. 1 to 4B FIG. 6 shows a diagrammatic side view of the arrangement of FIG. 3 in use, FIG. 7 represents in graphic form a summary of results compared to those obtained with a treadmill on the same group of patients, FIG. 8 shows graphically the changes in an Ankle Brachial Pressure index following exercise on a treadmill, and FIG. 9 shows graphically the changes in Ankle Brachial Pressure index following exercise on the device of FIGS. 1 to 3.

With reference to FIGS. 1 and 2 of the accompanying drawings the main components of the standardizable resistance means are a pressure plate (1) supported on a base frame (2) which also accommodates a tension spring (3). The pressure plate (1) is generally planar and extends upwardly from the base frame (2) and is provided at its lower end with an axle (12) journalled for rotation in an axle stand (13) forming part of the base frame (2). A heel plate (11) may optionally be provided, which extends normal to the plane of the pressure plate (1) at or adjacent the axle (12). Extending from the axle (12), generally downwardly and rearwardly as viewed in the arrangement of FIG. 1, is a fulcrum piece (19) terminating in a fulcrum pin (9) for connection with the tension spring (3). The tension spring (3) extends longitudinally of the base frame (2) towards the rear (14) thereof.

Situated at the rear (14) of the base frame (2), and extending therethrough, is a tension controller (4) which comprises a screw threaded member terminating at its remote outer end in an adjuster wheel (5). Riding on the tension controller (4) is a tension block (6) provided with an attachment for the spring (3) whereby a hook at the rear end of the spring (3) contacts the tension block (6) and is secured thereto by means of pin (7). The tension block is associated to the exterior of the device with a range of values, for example "high", "medium" and "low", which allows the paramedic to set the pressure required to actuate the plate.

In use an extremity of an upper or lower limb is placed upon the pressure plate (1) and the indicator (8) is set to an appropriate value for the patient concerned. The patient is then invited either to depress the plate a set number of times, or to depress the plate an indeterminate number of times for a certain period or until the muscle groups under test become significantly fatigued. Prior to operation of the device the flow rate in the most appropriate artery is recorded on a resting basis and is recorded again when the group of muscles have been satisfactorily fatigued. If the peripheral flow rate remains much the same then the patient's pain is more likely to be orthopaedic in origin, whereas if the blood flow is significantly reduced the problem is most likely to be vascular in origin and require further investigation.

FIG. 2 shows an alternative arrangement in accordance with the present invention. Like parts have been designated with like annotations except when they differ. In particular the pressure plate (1) as shown in FIG. 1 has been provided with an elongate slot (18) extending past the axis of rotation of the axle (12). Slidingly located in the slot (18) is a wing nut and bolt assembly (17) which is utilised to clamp a moveable heel plate (11) to the planar surface of the pressure plate (1) by means of flange (16) through which the wing nut and bolt assembly (17) passes. In other respects the device is substantially the same as shown in FIG. 1.

It is sometimes desirable to particularly exercise the muscles which control the attitude of the foot relative to the leg. If it is desired to do this the heel plate (11) may be moved downwardly relative to the arrangement shown in FIG. 2 such that the heel is normally, in the at rest position, inferior to the axis rotation of the axle (12). Accordingly, work can only be effected by rotation of the ankle if the heel is located against the heel plate (11). This means that fatigue can be fairly rapidly induced in the muscles controlling the ankle since the motion imposed on the patient particularly exercises this group of muscles.

In the alternative, the heel plate may be moved to be coincident with, or superior to, the axis of rotation of the axle (12) in the at rest condition. In this condition the calf and knee muscles will tend to be exercised rather than the ankle muscles. Blood flow rate determinations utilising the standardizable resistance means in accordance with the present invention can be made with a Dopplex Vascular Blood Flow Monitor in accordance with manufacturer's directions.

FIG. 3 shows a standardizable resistance means (20) of an alternative configuration but which operates on the same principle. The standardizable resistance means (20) comprises a base frame (22) supporting a cylinder portion (22). The frame (22') terminates at its forward end (25) in an axle stand portion (33) provided at its upper most portion with an axial (32). Axle (32) supports pressure plate (21) provided at its lower end with a heel plate (31). The heel plate (31) is moveable relative to the axle (32) if desired, but generally is positioned so that with the patient's foot on pressure plate (21) and the patient's heel resting on the heel plate (31), the longitudinal axis of the patient's leg passes close to or through the axle (32). The pressure plate (21) is also provided with an extension handle (27) which is extendable from the position shown in FIG. 3 to an extended position at a variable hight where it may be secured by means of a thumb screw or other convenient means (not shown). A saddle (28) is optionally provided for use with the resistance means (20) such that it clips on to the cylinder portion (21) prime and is provided with an upstanding elbow rest (29). It will be observed that with the handle (27) extended and with the saddle (28) correctly positioned on the cylinder (22') the arm can be exercised in the same way that the foot is exercised normally.

The cylinder (21') is provided at a remote end (24) with tension controller (26). The tension controller (26) is arranged such that it provides a reasonably accurate reflection of the tension applied to spring (23). Spring (23) extends from the rear end of the cylinder (24) to the forward end of the cylinder (25) and is secured at both ends by means of generally annular spring retainers. Either or both of the spring retainers are provided with a permanent magnet for cooperation with a hall effect device (not shown), positioned suitably on the internal face of the cylinder (22'). The hall effect device is connected to outputs (30) by means of this device and an output signal is thus generated each time the spring is elongated to a predetermined degree. This provides a means of counting, and because the extension of the spring by a set amount is known, work done can be readily calculated.

As stressed in the foregoing discussions the arrangements of FIGS. 1 to 3 can be utilised by for example a general practitioner to ascertain whether or not a problem of leg pain experienced by a patient is vascular in origin merely by taking a first reading with a Doppler probe and repeating the reading after an exercise period. As explained before the absence of blood flow pressure will indicate a vascular problem and hence indicate the need for specialist care.

However the arrangement of FIG. 3 particularly provides also a simple and effective mechanism whereby all non-invasive investigations related to the diagnosis and surveillance of patients with peripheral vascular disease can be computer linked and automated.

Blood flow rate determinations utilising the standardizable resistance means in accordance with the present invention can be made with a Dopplex Vascular Blood Flow Monitor in accordance with manufacturer's directions.

Accordingly, the invention provides in one aspect a diagnostic apparatus comprising a standardizable resistance means to resist a force applied thereto by a group of limb muscles during exercise, and test means for physiologically measuring blood flow measured before and after exercise with the standardizable resistance means. If there is a vascular obstruction in the limb the blood flow will markedly fall or even reach zero.

Calculations can also be effected of the work done to reach ischaemic pain and this can be equated to the distance that the patient is actually able to walk, which is more accurate than the values presently obtainable. Tables can be prepared for the normal and the diseased, equating work done on the device in accordance with the present invention with distance actually walked and hence values can be given in mobility ranges if desired.

Measurements can also be made of the time to recover after exercise-induced ischaemia. Thus it is possible, utilising the device of the present invention, to make more than one measurement after exercise, whereas with prior art treadmill arrangements only one measurement is actually made because of the time delay in getting the patient to the couch. In some circumstances it is possible to take measurements of resting limbs actually during exercise, which can provide significant information where disease is not localised to the limb under test.

The resistance means is preferably such as to resist multiple motions to induce fatigue by using up oxygen and available nutrients in the limb that has an inadequate blood supply.

As stated previously measurements in blood flow and blood pressure may be effected utilising a Doppler probe. To this end and for a full investigation on a patient's vascular status the following investigations may be performed:

1. pre-exercise Doppler pressure and flow,
2. pre-exercise transcutaneous oxygen,
3. post-exercise Doppler pressure and flow after exercise induced fatigue or claudication,
4. post-exercise transcutaneous oxygen,
5. work done calculations as a function of the outputs from the standardizable resistance means and
6. recovery time.

As indicated previously the difficulty of utilising a Doppler probe is that although the position of a particular artery can be located pre-exercise it is difficult to be sure that the correct position for the hand hold Doppler probe has been found, particularly and when vascular flow is at low or zero levels. To this end the applicants have developed the arrangement of FIGS. 4A and 4B.

FIG. 4A shows a temporarily adherent probe (40) which is adapted, by means of skin contact member (41) for location at a precisely defined spot on the skin surface. The skin contact member (41) may be held in position by means of an adhesive or by means of a resilient member about the limb, for example. The underside of the skin contact member may be provided with a high friction surface or with a weakly adhesive layer if necessary.

The probe (40) is provided with an upstanding housing (43) which surrounds a removable transducer assembly (49) provided with an input and output connector portion (42). The transducer assembly (49) includes a pair of transducers; embedded in resin; transducer (44) being angled at 60° to the perpendicular and transducer (45) being perpendicular to the skin surface. The transducers (44) and (45) and the resin in which they are embedded are spaced inwardly of the skin contact surface level so as to provide a space for a gel layer (48) to provide an intimate contact between the transducer assembly (49) and skin.

The transducer (44) being angled at 60° is adapted to measure flow rate through a target vessel, whereas transducer (45) is arranged to measure pressure therein.

With reference to FIG. 4B the arrangement in accordance to the present invention is similar to that shown in FIG. 4A with the exception that transducer (46) is adapted for rotation or oscillation about a central point (47). In other respects the housing is similar to that of FIG. 4A but includes actuation means (not shown). such as a small electric motor or an electromagnetic oscillator. It will be appreciated that where, for example, an oscillator is utilised the oscillation will be over the 60° between perpendicular and an angle of 60° to the perpendicular, and that means are provided to output a signal at each change of direction of the oscillation thereby providing flow and pressure outputs. It is envisaged that a cycle of about one second will be necessary for this to occur.

As is shown in FIG. 5 the arrangements of FIGS. 3, 4A and 4B can be utilised together to provide an automated read out from the standardised resistance means (20). The operation of this is best shown in FIG. 6. As is shown in FIG. 5 the Doppler probe of FIGS. 4A or 4B are positioned on a patient's leg as shown, for example, in FIG. 6. At the same time an automatically inflatable cuff connected to port B of a computer (36) is disposed about the patient's leg (50). The outputs from probe (40) are connected to a port A of the computer (36) while recording means (34) associated with the standardised resistant means (20) is connected to port C of the computer (36).

In use the patient is required to lie flat and be relaxed for about five minutes until the pulse returns to normal. Preferably a sphygmananometer cuff is disposed about an arm and inflated. A Dopplex probe held between the forefinger and thumb at 45° angle is disposed over the brachial pulse. The cuff is inflated until doppler sound disappears and slowly reflated until the sound returns. This gives a brachial systolic pressure (BSP).

Ankle systolic pressure (ASP) is then found by utilising a Doppler probe to locate the dorsalis pedis or posterior tibial pulse.

The cuff is disposed about the leg just above the ankle and inflated. The pulse is located with the Doppler probe and the cuff is inflated until the Doppler sound disappears and slowly deflated until the sound returns. This gives a pressure reading. These two readings may be utilised to provide an ankle pressure index by dividing the ankle pressure reading by the branchial pressure reading. A normal ankle pressure index (API) is equal to or greater than one whereupon it is safe to apply compression therapy. When using the computer and printer, the pre-exercise wave form of the vascular flow rate and/or pressure are recorded.

It will be observed that with the in situ probes (40) as previously described it is only necessary to locate the dorsalis pedis or posteria tibial pulse on the first occasion and then to fix the fixed probes in situ. It is not then necessary to find the pulse again when pulse rates are low. This may be conveniently effected by marking the said pulse point with a marker pen, positioning a housing as shown in FIG. 4A and subsequently correctly orientating a transducer assembly (49) in said housing (40).

To commence testing the patient is required to sequentially depress the pressure plate (21) shown in FIG. 6 either by a set member of times, or usually over a set period of time or until claudication occurs. The tension controller (26) is adjusted to a value suited to the patient and the value read from the controller (26) may be input into the computer to give an indication of work done. The operation of the pressure plate (21) causes the permanent magnet associated with the spring (20) to operate the hall effect device each time the pressure plate (21) is fully depressed, thereby giving a count of a number of depressions achieved. Work done therefore by each patient may be readily measured and recorded for future comparison. During the test period the patient may be requested to cease movement of the leg so that intermediate determinations of the vascular flow may be rapidly made and input into the computer via port A.

The present invention therefore provides a portable space saving device. The arrangement is suitable for use by leg or arm muscles. The angle of the foot plate may be adjustable, as may be the arc travelled by the foot plate. The heel plate may be adjustable to ensure that the foot is, as far as is possible, in a standardised position.

By use of the arrangements in accordance to the present invention the measurement of exercise is totally variable depending upon the abilities of the patient and allows for patients to provide accurate data according to severity of symptoms without loss of information. An LED display can be provided to indicate Kilogram loading and cumulative total number of flexions. These outputs can be input into a suitably programmed computer.

It has been found that the drop in Doppler pressure recorded at the ankle during exercise with the devices in accordance to the present invention is an improvement upon the values achievable with the treadmill devices alluded to earlier in the Specification.

In the present invention the branchial blood pressure and pulse rate do not significantly change with exercise. With the treadmill there is an increase in blood pressure, pulse rate and cardiac output with exercise, for example:

TABLE 1

|  | RESTING PRESSURE | POST-EXERCISE TREADMILL | POST EXERCISE STRESST'ER |
| --- | --- | --- | --- |
| Brachial | 150 | 180 | 150 |
| Dorsial Pedis | 100 | 40 | 40 |
| Pressure Index | 0.66 | 0.22 | 0.27 |

This represents an inaccuracy of at least 5% between the Treadmill and the device of the invention (Stresst'er registered trade mark).

When utilising the treadmill there is a delay time occasioned by the movement of the patient from the treadmill to a couch for axle measurement to be performed. This is on average between 45 seconds and one minute. There is no delay time utilised in the arrangement of the present invention. The result of this may be seen in table two.

TABLE 2

| Device of invention; measurement made at time 0 = | 40 mm Hg. |
| --- | --- |
| Pressure Index = | 0.27 |
| Treadmill measurement made at time 1 min. | 58 mm Hg. |
| If B.P. = 150, Pressure Index = | 0.38 |
| If B.P. = 180, Pressure Index = | 0.32 |

Accordingly whether or not there is a rise in branchial pressure, or not there is a gross error created by the above delay of one minute which may represent in accuracy of as much as 20%. The recovery time which is a valuable index score is about 5 minutes on average. It will be appreciated that in the treadmill one minute of recovery time has already occurred before measurement is made that this represents an error of 20%.

A post exercise index is valuable in management scoring systems. 40% to 45% of patients cannot use the treadmill at all or can only do so inadequately. Added to this there is an inaccuracy of 5% to 20% in the measurement which means post exercise data is of limited use when obtained from the treadmill in 50% to 70% of cases. Inadequate data using the present invention only occurs in 2% to 5% of cases.

This is shown in FIG. 7 which shows a summary of the results of clinical data. These results clearly show that errors incurred by the time delay in moving the patient from the treadmill to the couch prior to taking ankle pressure readings with Doppler equipment is highly significant. The arrangement of the present invention therefore provides a more accurate diagnosis of the severity of symptoms and is particularly useful in patent surveillance. These results are confined in the following

EXAMPLE

Two groups of patients were studied: 10 healthy volunteers (5 male, and 5 female, age range 26–36 ys, means 28.3 ys), were exercised on the treadmill for 10 minutes, and then after full recovery on the selective exercise device for ten minutes. These patients acted as the control group. The second group were 35 patients, suffering from intermittent claudication who had not undergone surgery, 22 were male and 13 were female, (age range 58–81 ys). Diabetic patients were excluded from the study because arterial calcification in these patients prevents accurate A.B.P.I. measurement. 6 of the original 35 claudicant patients were unable to use the treadmill, and were therefore tested separately from the main study using the selective exercise device only. The remaining 29 claudicant patients were tested using both the treadmill and the selective exercise device of the invention. Each patient underwent resting Doppler arterial assessment of each lower limb, including measurement of pedal arterial occlusion pressures in each foot. A.B.P.I. measurements were performed with the handheld "Dopplex" Doppler ultrasound (Huntleigh Technology Plc). using the "Dopplex reporter" computer programme. The brachial arterial pressure was also measured, and A.B.P. I.s were calculated.

Exercise of the Treadmill was standardised at a speed of 4 kilometres per hour, at a gradient of 10%. The patients were asked to walk until claudication was apparent in either leg, and had become severe enough for them to stop walking. The treadmill was then stopped, and the patient was asked to return as quickly as possible to the couch. The time between stopping the treadmill and the first possible Doppler measurement was recorded. Thereafter A.B.P.I.s were measured at 1,3,5,8 and 10 minutes post-exercise, and at 15 minutes post-exercise if the A.B.P.I.s had failed to return to resting levels. The pulse rate and brachial arterial pressure were also measured at these time intervals post-exercise, and the Ankle Brachial pressure indices were calculated. The patients were allowed to recover fully from the treadmill exercise as judged by the return of resting A.B.P.I.'s in the lower limbs, and the return of pulse and blood pressure to resting values.

Next, each patient was asked to plantarflex the foot against the resistance provided by the selective exercise device of the invention, whilst keeping the knee joint fully extended.

This allowed selective contraction of the calf muscle groups only. Repeated relaxation and contraction of the calf muscle group induced claudication in the leg of the patient. The patient was asked to persist until the claudication was of similar intensity to that experienced whilst on the treadmill.

The patient was then asked to stop exercising, and the A.B.P.I.'s, the systolic blood pressure and the pulse rate were measured immediately, and at 30 sec, 1,3,5,8 and 10 minutes post exercise, and thereafter at 5 minute intervals until the A.B.P.I.'s had reached resting levels. The pedal arterial occlusion pressures were measured using standard blood pressure cuffs, and sphygmomanometer. The occlusion pressure being deemed to have been reached when the Doppler signal from the artery in question reappeared after reducing the cuff pressure around the ankle. The total exercise times on the treadmill and on the selective exercise device, were also recorded for each patient.

The resistance of the selective exercise device could be varied between 10 and 20 Kg. In this study the resistance was adjusted to the individual patient so that the selective exercise device could be operated without undue effort.

RESULTS

In the first (control) group the total number of limbs rested was 20. In this group the pre, and post-exercise A.B.P.I.s showed no significant difference either on the treadmill or the selective exercise device (P>0.1 Student's t test). In the second (claudicant) group, the total number of lower limbs tested was present in this group.

TABLE 3

| RISK FACTOR FOR ARTERIAL DISEASE | NUMBER OF PATIENTS AFFECTED |
| --- | --- |
| SMOKER/EX-SMOKER | 20 |
| HYPERTENSIVE (Treated and untreated) | 15 |
| HYPERLIPIDAEMIC | 7 |

Brachial blood pressure and pulse rate values before and after exercise.

The mean resting brachial blood pressure for the claudicant patients was 142 mmHg (S.D. 13 mmHg, range 15–175 mmHg), and the mean pulse rate was 72 beats per minute (S.D. 9.1, range 55–98 beats per minute).

The mean brachial blood pressure 1 minute following exercise on the treadmill was 177 mmHg (S.D. 11 mmHg), range 120–215 mmHg. The mean pulse rate was 141 beats per minute (S.D. 13.6, range 125–170 beats per minute).

The mean brachial blood pressure immediately following selective exercise was 146 mmHg (S.D. 15 mmHg, range 120–180 mmHg). The mean pulse rate was 76 beats per minute (S.D. 11.7, range 74–106 beats per minute).

There was no significant difference between the mean resting brachial blood pressure and the mean brachial blood pressure immediately after exercise on the selective exercise device (P<0.1, Student's t test).

Comparison of the mean resting brachial blood pressure and the mean brachial blood pressure 1 minute after cessation of exercise of the treadmill, was however significant (P<05, Student's t test).

Comparison of the pulse rates at rest with the pulse rates after exercise with the selective exercise device, showed no significant difference (P>0.1, Student's t test). Comparison of the pulse rates at rest with the pulse rates after exercise on the treadmill, were significantly different (P<0.05 Student's t test).

The post-exercise pedal arterial pressure was expressed as the A.B.P.I. Comparison of the initial post exercise A.B.P.I.s demonstrates no significant difference between the selective exercise and the treadmill (t=>0.05). It should be noted that the mean time taken for the patients to leave the treadmill after exercise, and lie on the examination couch ready for measurement of the pedal pressures, was 42 seconds (range 29–52 seconds) phase. For this reason it was decided to measure the initial A.B.P.I. at 1 minute following exercise of the treadmill. Measurement of the initial A.B.P.I. using the selective exercise device was possible immediately after exercise.

The change in A.B.P.I. is plotted against time after exercise, on the treadmill (FIG. 8) and on the selective exercise device (FIG. 9).

The time required to induce claudication that prevented further exercise, was a mean of 8.1 minutes (range 5.3–12.2 minutes) using the selective exercise device, and a mean of 4.4. minutes (range 2.2–5.8 minutes) using the treadmill. These were significantly different P=<0.05 (Student's t test).

The time for the A.B.P.I. to reach resting levels following exercise was shorter for the selective exercise device (mean 9.1 mins range 7.5–11.2 minutes) than for the treadmill (mean 12.6 mins S.D. ·2.2). However this difference was not significant.

6 patients were examined separately from the study because they were unable to use the treadmill. Table 4 below shows the reasons for the patients being unable to use the treadmill.

TABLE 4

| DISBABILITY | NUMBER OF PATIENTS |
| --- | --- |
| Unstable Angina | 4 |
| Unilateral Amputee | 1 |
| Ischaemic Foot ulceration | 1 |

5 of 6 patients were able to use the selective exercise device. The patient with ischaemic foot ulceration was unable to tolerate any pressure on the foot. FIG. 3 demonstrates the mean change in A.B.P.I. at 0 secs., 30 secs., 1 min., 3 min., and 5 mins., post-exercise for these five patients.

The demonstration of a fall in the A.B.P.I. following exercise has been used in the diagnosis and surveillance of arterial disease of the lower limb for nearly 20 years. The treadmill until now has been the only standardised method of exercise in routine use. Attempts at exercising the calf muscles without any resistance, to induce claudication have been shown to produce submaximal decreases in ankle Doppler pressures, as have procedures that cause postocclusive reactive hyperaemia. The selective exercise device exercises the calf muscles against a known resistance and depresses the ankle Doppler pressures to a similar degree as the treadmill and is the first effective alternative in this respect. The selective exercise device allows immediate measurement of the A.B.P.I. post-exercise unlike the treadmill where there is an unavoidable lag phase (mean 42 seconds range 29–52 seconds). Because of this lag phase, which may be variable, it renders the post-exercise data obtained on the treadmill more prone to be unreliable and non-reproducible.

6 of the patients were unable to use the treadmill due to angina previous amputation, or ulceration of the foot. We were able to measure post-exercise falls in A.B.P.I.s. with the selective exercise device in all these patients except one who had painful pedal ulceration.

The selective exercise device may be used to evaluate asymmetric vascular occlusive disease, which may be difficult using the treadmill because the worst leg will prevent maximal stress to the less affected leg. This may be of practical importance when planning intervention by percutaneous angioplasty, stenting, atherectomy, or by operation.

Results to date have demonstrated that by selectively exercising the calf muscles in the lower limb against a known resistance, an immediate post-exercise A.B.P.I. can be obtained and recovery measurements can be made at accurate time intervals from the cessation of exercise. This recovery time may provide additional information on the severity of the vascular disease. With the selective exercise device there is no alteration in brachial blood pressure or pulse rate.

In contrast during treadmill exercise on there is a significant alteration in brachial blood pressure and pulse rate. These physiological changes may also contribute to the unreliability of the post-exercise Doppler data, and there may be many other variable effects when the whole patient is exercised. We believe that selective exercise will make post-exercise data more reliable and reproducible.

We claim:

1. A diagnostic apparatus comprising a resistance device to resist a force applied thereto by a selected group of limb muscles during exercise, and test means for physiologically measuring a biological component resultant from said limb exercise, wherein the resistance device comprises a pressure plate pivoted about an axle, spring means operatively connected to said plate to bias the plate to an at rest position, and adjustment means for preloading the spring means, characterized by means for indicating spring means preload, such that the spring means can be preloaded to a desired value, whereby in use the plate is reciprocatable by a limb against the spring means bias to induce fatigue or claudication on a basis which is standardizable between patients.

2. An apparatus according to claim 1 wherein said biological component is selected from one or more of blood flow, blood pressure, transcutaneous oxygen, and lymphatic clearance rate.

3. An apparatus according to claim 1 wherein the test means is selected from a Doppler device to measure blood flow, an oximeter to measure transcutaneous oxygen values, means for measuring compartmental pressures, and means for measuring leg volume.

4. An apparatus according to claim 1 wherein the standardizable resistance means comprises a spring biased pivoted plate provided with heel plate.

5. An apparatus according to claim 4 wherein the relative position of the heel plate is moveable.

6. An apparatus according to claim 1 wherein the test means is an in situ Doppler device adapted to measure both blood flow and blood pressure.

7. An apparatus according to claim 6 wherein the axle is supported on a base which base, encloses and/or supports the adjustment means.

8. An apparatus according to claim 6 wherein the adjustment means is a tension spring and comprises a screw threaded block connecting a screw thread to the tension spring, and wherein the apparatus also includes indicator means to preset a desired tension loading in the spring.

9. An apparatus according to claim 6 wherein the means for physiologically testing blood flow is a Doppler ultrasound blood flow and pressure monitoring device.

10. An apparatus according to claim 6 wherein the arc of travel of the pressure plate is adjustable and the apparatus provides means indicative of the load applied and wherein the spring means is operatively associated with a signal generating means indicative of each movement whereby work done can be readily calculated.

11. An apparatus according to claim 10 wherein the spring means is associated with a permanent magnet and a hall effect sensor thereby to generate an output signal for each completed stroke of the pressure plate.

12. An apparatus according to claim 1 wherein the pressure plate further comprises an extendible handle and a base which supports the axle comprises an elbow restraint means on an upper surface thereof.

13. A Doppler transducer assembly comprising a housing including a skin contact surface, said housing being adapted to be releasably affixed to the skin; said housing supporting a Doppler transducer means adapted to output a signal when positioned at each of a plurality of stations, one of said signals being indicative of blood pressure, and another of said signals being indicative of blood flow.

14. An assembly according to claim 13 wherein the Doppler transducer means comprises at least two fixed transducers, the first of said transducers being positioned substantially perpendicular to the skin contact surface of the housing, and the second of said transducers being fixed at a predetermined angle relative thereto.

15. An assembly according to claim 14 wherein the predetermined angle of the second transducer is at or about 60° to the skin contact surface of the housing.

16. An assembly according to claim 13 wherein the Doppler transducer means comprises a transducer rotatable about its horizontal axis or oscillatable through a predetermined angle, said transducer being adapted to output a first signal indicative of blood pressure and a second signal indicative of blood flow.

17. An assembly according to claim 16 wherein the first signal is derived from a transducer positioned substantially perpendicular to the skin contact surface of the housing, and the second signal is derived from the transducer when at an angle substantially of 60° relative to the skin contact surface of the housing.

18. An assembly according to claim 16 wherein the transducer is driven by an electric motor or is caused to oscillate by electromagnetic means.

19. An assembly according to claim 13 wherein the transducer means is provided with a flow line indicator means to allow flow and pressure transducers to be correctly orientated relative to an artery wherein blood pressure and flow are being measured and the housing while fixed.

20. An assembly according to claim 13 wherein the head of the transducer assembly is recessed from the plane of the skin contact surface housing thereby to accommodate a Doppler wave gel.

21. An assembly according to claim 13 wherein the housing is releasably retained upon the skin and wherein the skin contact surface of the housing is provided with a high friction or adhesive surface.

22. An assembly according to claim 21 wherein the housing is retained on the skin by resilient means extending about a body part.

23. An assembly according to claim 13 including a sphygmomanometer cuff, the assembly being constructed and arranged whereby at periodic intervals during diagnosis said cuff is inflated in response to a predetermined cuff control signal to allow blood pressure and blood flow rate to be automatically recorded.

24. An assembly according to claim 13 wherein the signals are computer controlled and analysed.

25. A method for the non-invasive diagnosis of peripheral vascular supply to a limb, which method comprises:

establishing a resting vascular pressure or flow rate, utilising the limb to repeatedly move a standardised resistance over a predetermined distance for a set period of time or until claudication occurs, and establishing a post exercise pressure or flow rate.

26. A method according to claim 25 wherein the limb is the leg and the pre- and post-exercise pressures are denoted by an ankle pressure index as hereinbefore set forth.

27. A method according to either of claims 25 or 26 wherein the vascular flow and/or pressure values are monitored during timed intervals during the exercise routine and wherein a cuff secured about the ankle is inflated at timed intervals during exercise thereby to allow vascular flow and pressure values to be monitored during short resting periods during exercise.

28. A method according to claim 25 further comprising oximetry determinations.

29. An apparatus according to claim 7, wherein the adjustment means is a tension spring and comprises a screw threaded block connecting a screw thread to the tension spring, and wherein the apparatus also includes indicator means to preset a desired tension loading in the spring.

30. An assembly according to claim 17 wherein the transducer is driven by an electric motor or is caused to oscillate by electromagnetic means.

* * * * *